United States Patent [19]

Lilje

[11] Patent Number: 4,479,904
[45] Date of Patent: Oct. 30, 1984

[54] REDUCTION OF NITROAROMATIC COMPOUNDS

[75] Inventor: Kenneth C. Lilje, Baton Rouge, La.

[73] Assignee: Ethyl Corporation, Richmond, Va.

[21] Appl. No.: 506,236

[22] Filed: Jun. 20, 1983

[51] Int. Cl.³ .......................................... C07C 121/78
[52] U.S. Cl. ................................................ 260/465 E
[58] Field of Search .................................... 260/465 E

[56] References Cited
U.S. PATENT DOCUMENTS 4,370,278  1/1983  Stahly et al. ................... 260/465 E

OTHER PUBLICATIONS

March, Advanced Organic Chemistry (McGraw-Hill, New York, 1977), pp. 1125-1126.

Primary Examiner—Dolph H. Torrence
Attorney, Agent, or Firm—Donald L. Johnson; John F. Sieberth; Patricia J. Hogan

[57] ABSTRACT

Aminoarylacetonitriles, such as 2-(4-amino-3-fluorobenzene)propionitrile, are prepared by (1) isolating the crude reaction product from a process wherein a nitroaromatic compound has been reacted with an alpha,alpha-disubstituted acetonitrile in an inert solvent and in the presence of a base so as to form a nitroarylacetonitrile and (2) subjecting that crude reaction product to reduction in the presence of active iron powder and an aqueous alkanol.

17 Claims, No Drawings

REDUCTION OF NITROAROMATIC COMPOUNDS

FIELD OF THE INVENTION

This invention relates to aminoarylacetonitriles and a process for preparing them.

BACKGROUND

As disclosed in U.S. Pat. No. 4,370,278 (Stahly et al.) and in copending applications Ser. Nos. 452,518 (Stahley et al. I), and 452,615 (Stahly), and 452,618 (Stahly et al. II), filed Dec. 23, 1982, and Ser. Nos. 487,038 (Lilje) and 487,039 (Lilje I), filed Apr. 21, 1983, it is known that nitroarylacetonitriles can be prepared by reacting a nitroaromatic compound with an alpha,alpha-disubstituted acetonitrile in an inert solvent and in the presence of a base—a reaction that appears to occur by a nucleophilic substitution mechanism and is therefore sometimes described in the references and herein as a nucleophilic substitution process.

It is also known that the nitroarylacetonitriles formed by the nucleophilic substitution process can be converted to the corresponding aminoarylacetonitiles by conventional methods of reduction, such as catalytic hydrogenation or the use of active iron powder; and Stahly et al. teach that the use of palladium-catalyzed hydrogenation is the preferred method of reduction.

Although satisfactory results have been obtained when a substantially pure nitroarylacetonitrile has been reduced by catalytic hydrogenation, as recommended by Stahly et al., erratic results, e.g., yields ranging from about 49-90%, have been encountered when that technique has been used for the reduction of the crude nitroarylacetonitriles prepared by nucleophilic substitution processes. It would obviously be desirable to find a reduction technique that could be used to provide consistently high yields of aminoarylacetonitriles from the crude nitroarylacetonitriles.

SUMMARY OF THE INVENTION

An object of this invention is to provide a novel process for preparing aminoarylacetonitriles.

Another object is to provide such a process wherein the aminoarylacetonitriles are prepared in consistently high yields from crude nitroarylacetonitriles.

These and other objects are attained (1) isolating the crude reaction product from a process wherein a nitroaromatic compound has been reacted with an alpha,alpha-disubstituted acetonitrile in an inert solvent and in the presence of a base so as to form a nitroarylacetonitrile and (2) subjecting that crude reaction product to reduction in the presence of active iron powder and an aqueous alkanol.

DETAILED DESCRIPTION

The crude reaction products that are reduced in accordance with the present invention are products obtained by reacting a nitroaromatic compound with an alpha,alpha-disubstituted acetonitrile in an inert solvent and in the presence of a base so as to form a nitroarylacetonitrile. The materials and reaction conditions used to prepare the crude reaction products can be any of the materials and conditions disclosed in Stahly, Stahly et al., Stahly et al. I, Stahly et al. II, Lilje, and/or Lilje I, the teachings of which are incorporated herein by reference. Thus, e.g.:

(1) the nitroaromatic compound may be any of a variety of nitroaromatic compounds bearing at least one nitro substituent on an aromatic ring having at least one replaceable hydrogen thereon and optionally bearing one or more inert substituents, such as halo, haloalkyl, alkoxy, haloalkoxy, etc., but is preferably a mononitrobenzene, such as nitrobenzene, the 2-, 3-, and 4-fluoronitrobenzenes, the corresponding chloro, bromo, and iodo compounds, etc., (2) the alpha,alpha-disubstituted acetonitrile may be any of a variety of such compounds which can be represented by the formula:

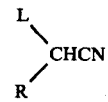

wherein L is a leaving group, preferably halo, more preferably chloro or bromo; and R is a hydrocarbyl or hydrocarbyloxyhydrocarbyl group, preferably such a group containing not more than 10 carbons, more preferably an alkyl group; but is most preferably an alpha-haloalkyl cyanide containing at least three carbons, such as 2-chloropropionitrile, 2-bromopropionitrile, etc., (3) the solvent may be any solvent that is inert under the conditions of the reaction but is generally a substantially anhydrous aprotic solvent, preferably a dipolar aprotic solvent, such as N,N-dimethylformamide, N,N-dimethylacetamide, etc., and (4) the base may be any base strong enough to activate the nitrile reactant but is generally an alkali metal compound, preferably an alkali metal hydride, hydroxide, or alkoxide, such as sodium or potassium hydride, hydroxide, t-butoxide, etc.

When the nitroaromatic compound and alpha,alpha-disubstituted acetonitrile have been reacted as in the aforementioned references, the reaction mixture is worked up, e.g., by the acidification, solvent extraction, washing, drying, filtration, and evaporation steps disclosed in those references, to isolate a crude reaction product that typically contains the desired nitroarylacetonitrile, some unreacted nitroaromatic compound, and by-products. The desired nitroarylacetonitrile, as taught in the references, is a 2-(nitroaryl)acetonitrile, such as 2-(4-nitrobenzene)propionitrile, 2-(3-fluoro-4-nitrobenzene)propionitrile, 2-(3-fluoro-2-nitrobenzene)propionitrile, 2-(3-chloro-4-nitrobenzene)propionitrile, etc.

In the practice of the present invention, it is the crude reaction product, rather than substantially pure nitroarlyacetonitrile, that is subjected to reducing conditions to form the aminoarylacetonitrile corresponding to the nitroarylacetonitrile. The reduction is accomplished by the use of active iron powder—a conventional technique mentioned in Stahly et al. and also taught, e.g., in March, *Advanced Organic Chemistry*, McGraw-Hill, (New York), 1977, page 1125. As is well known, this technique involves the use of iron powder that is activated by an acid, usually an acid having a dissociation constant of at least $1.7 \times 10^{-5}$ at 25° C., such as acetic, hydrochloric, sulfuric, nitric, etc. The acid employed to activate the iron may be dilute, as in Stahly et al., but is preferably concentrated. In a particularly preferred embodiment of the invention, the acid is hydrochloric acid, most preferably concentrated hydrochloric acid.

The iron is activated with the acid prior to being contacted with the reaction mixture, and the reduction is accomplished by hydrogenating the crude reaction product at an elevated temperature in the presence of an amount of aqueous alkanol, e.g., methanol, ethanol, other alkanols containing 1-6 carbons, etc., sufficient to dissolve the crude reaction product. It is possible to conduct the invention by accomplishing the activation of the iron in the presence of the aqueous alkanol, but it is generally preferred to delay adding the aqueous alkanol until the activation has been effected: the time required for conducting the reduction generally being longer when the aqueous alkanol has been added prior to the iron's being activated. The temperature employed for the reduction is usually reflux temperature, preferably about 80° C., and the amount of water in the aqueous alkanol is ordinarily such as to provide a water-/alkanol mol ratio in the range of about 1-4/1, preferably about 3-4/1. The preferred alkanol for use in the process is ethanol.

The reduction process is conducted for a time sufficient to reduce a substantial number of the nitro groups in the crude reaction product to amino groups, ordinarily for about 1.5-4, e.g., about 2.5, hours. Reduction of the crude reaction product in accordance with the present invention typically results in a 90-98% yield of the desired amino compound when the reaction is conducted for at least 2.5 hours.

The amino compound produced by the process of the invention may be converted to other products, as taught in the aforementioned references, either before or after being separated by known techniques from the other components of the reaction mixture.

The following example is given to illustrate the invention and is not intended as a limitation thereof. In the example, the crude reaction product employed as a starting material was a product obtained by reacting substantially equimolar amounts of 2-fluoronitrobenzene and 2-chloropropionitrile with one another in N,N-dimethylacetamide (DMAC) and in the presence of a base, as in Stahly et al.

EXAMPLE

A suitable reaction vessel was charged with 45 g (2.5 mols) of water, 50.4 g (0.9 mol) of iron powder, 30.4 g (0.66 mol) of ethanol, and 4 g (0.039 mol) of concentrated hydrochloric acid and heated at 70° C. for 5 minutes. Then 29.3 g (0.15 mol) of 2-(3-fluoro-4-nitrobenzene)propionitrile (FNPN) were added over a period of 15 minutes as a crude reaction product comprising a solution containing 12.2% by weight of the FNPN, 26.2% by weight of DMAC, and 24.5% by weight of ethanol. The reaction mixture was refluxed for four hours, after which 14 g of 10% sodium hydroxide were added, followed by 5 g of 25% sodium carbonate monohydrate. The mixture was then stirred and refluxed for one hour, filtered hot, washed with 157 g of hot ethanol, and rotary evaporated to provide 115.7 g of residue. Analysis by vpc showed that the reaction resulted in a 98% yield of the desired 2-(4-amino-3-fluorobenzene)propionitrile (AFPN).

It is obvious that many variations may be made in the products and processes set forth above without departing from the spirit and scope of this invention.

I claim:

1. In a process for preparing a 2-(aminoaryl)acetonitrile by (a) reacting a nitroaromatic compound with an alpha,alpha-disubstituted acetonitrile in an inert solvent and in the presence of a base and (b) reducing the 2-(nitroaryl)acetonitrile thus obtained, the improvement which comprises:
   (1) isolating the crude reaction product of the nitroaromatic compound/alpha,alpha-disubstituted acetonitrile reaction and
   (2) subjecting that product to reduction in the presence of iron powder and an aqueous alkanol.

2. The process of claim 1 wherein the nitroaromatic compound is a mononitrobenzene.

3. The process of claim 2 wherein the mononitrobenzene is nitrobenzene.

4. The process of claim 2 wherein the mononitrobenzene is 2-fluoronitrobenzene.

5. The process of claim 2 wherein the mononitrobenzene is 2-chloronitrobenzene.

6. The process of claim 1 wherein the alpha,alpha-disubstituted acetonitrile is an alpha-haloalkyl cyanide containing at least three carbons.

7. The process of claim 6 wherein the alpha-haloalkyl cyanide is 2-chloropropionitrile.

8. The process of claim 1 wherein the active iron powder is the product obtained by activating iron powder with hydrochloric acid.

9. The process of claim 1 wherein the aqueous alkanol is an aqueous alkanol containing 1-6 carbons.

10. The process of claim 9 wherein the aqueous alkanol is aqueous ethanol.

11. The process of claim 10 wherein the aqueous ethanol contains about 1-4 molar proportions of water per molar proportion of ethanol.

12. The process of claim 11 wherein the aqueous ethanol contains about 3-4 molar proportions of water per molar proportion of ethanol.

13. The process of claim 1 wherein the reduction is conducted at reflux temperatures.

14. The process of claim 13 wherein the reduction is conducted at a temperature of about 80° C.

15. In a process for preparing 2-(4-amino-3-fluorobenzene)propionitrile by (a) reacting 2-fluoronitrobenzene with 2-chloropropionitrile in an inert solvent and in the presence of a base and (b) reducing the 2-(3-fluoro-4-nitrobenzene)propionitrile thus obtained, the improvement which comprises:
   (1) isolating the crude reaction product of the 2-fluoronitrobenzene/2-chloropropionitrile reaction and
   (2) subjecting that product to reduction in the presence of active iron powder and an aqueous alkanol.

16. The process of claim 15 wherein the crude reaction product is reduced at reflux temperatures in the presence of iron powder that has been activated with hydrochloric acid and in the presence of an aqueous ethanol containing about 1-4 molar proportions of water per molar proportion of ethanol.

17. The process of claim 16 wherein the crude reaction product is reduced at a temperature of about 80° C. and the aqueous ethanol contains about 3-4 molar proportions of water per molar proportion of ethanol.

* * * * *